(12) United States Patent
Kuriki et al.

(10) Patent No.: US 9,677,992 B2
(45) Date of Patent: Jun. 13, 2017

(54) CORROSION PROTECTION PERFORMANCE DEGRADATION DETECTION SENSOR, HOT-WATER SUPPLY HEATING SYSTEM, AND FACILITY APPARATUS

(75) Inventors: Hironori Kuriki, Chiyoda-ku (JP); Hideyuki Morimura, Chiyoda-ku (JP); Kazuhiro Miya, Chiyoda-ku (JP); Seiji Furukawa, Chiyoda-ku (JP)

(73) Assignee: Mitsubishi Electric Corporation, Tokyo (JP)

(*) Notice: Subject to any disclaimer, the term of this patent is extended or adjusted under 35 U.S.C. 154(b) by 93 days.

(21) Appl. No.: 14/355,977

(22) PCT Filed: Apr. 5, 2012

(86) PCT No.: PCT/JP2012/002386
§ 371 (c)(1),
(2), (4) Date: Jun. 16, 2014

(87) PCT Pub. No.: WO2013/065207
PCT Pub. Date: May 10, 2013

(65) Prior Publication Data
US 2014/0326340 A1 Nov. 6, 2014

(30) Foreign Application Priority Data

Nov. 2, 2011 (JP) .................. 2011-241374

(51) Int. Cl.
*G01R 27/08* (2006.01)
*G01N 17/02* (2006.01)
(Continued)

(52) U.S. Cl.
CPC ............ *G01N 17/02* (2013.01); *C02F 1/686* (2013.01); *C23F 11/00* (2013.01); *C23F 11/08* (2013.01);
(Continued)

(58) Field of Classification Search
CPC ...... G01N 27/06; G01N 17/02; G01N 27/026; G01N 27/021
(Continued)

(56) References Cited

U.S. PATENT DOCUMENTS 2,374,088 A * 4/1945 Fontana ................. G01N 17/02
204/404
3,361,150 A * 1/1968 Horner ................... F22B 21/06
204/404
(Continued)

FOREIGN PATENT DOCUMENTS

JP 62-207898 9/1987
JP 63-93882 4/1988
(Continued)

OTHER PUBLICATIONS

International Search Report issued Jul. 17, 2012, in PCT/JP12/002386 filed Apr. 5, 2012.
(Continued)

*Primary Examiner* — Craig Schneider
*Assistant Examiner* — Angelisa L Hicks
(74) *Attorney, Agent, or Firm* — Oblon, McClelland, Maier & Neustadt, L.L.P.

(57) ABSTRACT

A corrosion protection performance degradation detection sensor includes a detection electrode that reacts with the corrosion inhibitor dissolved in the solvent and forms on a surface thereof an electrode surface film which inhibits corrosion, a counter electrode that is disposed so as to face the detection electrode, and an AC power supply that applies an AC voltage between the detection electrode and the counter electrode. A change in concentration of the corrosion inhibitor in the solvent is detected, on the basis of a change in impedance of the electrode surface film formed on the surface of the detection electrode.

12 Claims, 5 Drawing Sheets

(51) Int. Cl.
| | |
|---|---|
| C23F 11/18 | (2006.01) |
| F24H 1/10 | (2006.01) |
| F24H 9/00 | (2006.01) |
| G01N 17/04 | (2006.01) |
| C23F 11/00 | (2006.01) |
| C23F 11/08 | (2006.01) |
| C02F 1/68 | (2006.01) |
| F24D 19/00 | (2006.01) |

(52) U.S. Cl.
 CPC .......... *C23F 11/18* (2013.01); *F24D 19/0092* (2013.01); *F24H 1/106* (2013.01); *F24H 9/0047* (2013.01); *G01N 17/04* (2013.01); *C02F 2209/00* (2013.01); *C02F 2303/08* (2013.01); *Y10T 137/85986* (2015.04)

(58) Field of Classification Search
 USPC ............... 324/700; 204/404; 205/775.5–777; 425/53
 See application file for complete search history.

(56) References Cited

U.S. PATENT DOCUMENTS

| | | | | |
|---|---|---|---|---|
| 3,592,212 | A * | 7/1971 | Schleimer | ............... C02F 1/685 137/88 |
| 3,721,258 | A * | 3/1973 | Dermiah | ................. F28C 1/003 137/101.25 |
| 4,266,187 | A | 5/1981 | Slough | |
| 4,460,008 | A * | 7/1984 | O'Leary | ................. G01N 27/06 137/5 |
| 5,972,198 | A * | 10/1999 | Takeuchi | ............... G01N 17/02 205/341 |
| 6,406,618 | B1 * | 6/2002 | O'Leary | ................... C02F 1/50 169/16 |
| 2004/0149663 | A1 * | 8/2004 | Nakanishi | ............. C02F 1/4674 210/98 |
| 2005/0183969 | A1 * | 8/2005 | Luopa | .................... G01N 17/02 205/775.5 |
| 2007/0163892 | A1 * | 7/2007 | Haridas | ................. G01N 17/04 205/776.5 |
| 2008/0017827 | A1 | 1/2008 | Ito et al. | |
| 2010/0155262 | A1 * | 6/2010 | Yepez | ................... G01N 17/02 205/775.5 |

FOREIGN PATENT DOCUMENTS

| | | |
|---|---|---|
| JP | 2-291952 | 12/1990 |
| JP | 3-160354 A | 7/1991 |
| JP | 5-126776 | 5/1993 |
| JP | 5-263276 | 10/1993 |
| JP | 6-323984 | 11/1994 |
| JP | 7-502830 | 3/1995 |
| JP | 9-268386 | 10/1997 |
| JP | 2000-329720 | 11/2000 |
| JP | 2010-16045 A | 1/2010 |
| WO | WO 94/12862 A1 | 6/1994 |
| WO | WO 2006/087809 A1 | 8/2006 |

OTHER PUBLICATIONS

Office Action issued on Nov. 23, 2015 in Chinese Patent Application No. 201280053461.4 with English translation.
European Office Action issued Jan. 2, 2017 for European Patent Application No. 12844952.7.
Office Action issued Apr. 14, 2015 in Japanese Patent Application No. 2013-541587 (with English language translation).
Nobuyasu Dohi, et al., "Inhibition Effects of Benzotriazole for Corrosion of Copper" The Journal of the Metal Finishing Society, vol. 24, No. 7, 1973, pp. 396-401 (with English Abstract).
Yoshiharu Matsuda, "Electrochemical Measurements Used in Studies of Bright Plating" The Journal of the Metal Finishing Society, vol. 34, No. 8, 1983, pp. 408-415 (submitting partial English translation only, reference previously filed).
Combined Office Action and Search Report issued Apr. 16, 2015 in Chinese Patent Application No. 201280053461.4 ( with English language translation and English translation of Category of Cited Documents).
Extended European Search Report issued May 19, 2015 in Patent Application No. 12844952.7.
F. El-Taib Heakal, et al., "Impedance studies of the Inhibitive Effect of Benzotriazole on the Corrosion of Copper in Sodium Chloride Medium" Corrosion Science, vol. 20, No. 7, Jan. 1, 1980, pp. 887-898.

\* cited by examiner

CORROSION PROTECTION PERFORMANCE DEGRADATION DETECTION SENSOR, HOT-WATER SUPPLY HEATING SYSTEM, AND FACILITY APPARATUS

TECHNICAL FIELD

The present invention relates to a corrosion protection performance degradation detection sensor that detects degradation of corrosion protection performance of a coolant (solvent) to which a corrosion inhibitor that inhibits corrosion of an anticorrosion target material used in an atmosphere containing moisture is added, a hot-water supply heating system, and a facility apparatus.

BACKGROUND ART

As a facility apparatus, such as a hot-water supply heating system and an air-conditioning system, there has been proposed a facility apparatus that suppresses corrosion by adding a corrosion inhibitor to coolant, in order to inhibit corrosion of a metal material, such as a pipe that forms a system. However, in this facility apparatus, when the concentration of the corrosion inhibitor decreases after long-term use or for any other reason, the corrosion protection performance of the coolant degrades. Thus, the corrosion of the metal material proceeds. Then, when the corrosion of the metal material proceeds, pitting occurs in the metal material, and thus through holes are created. This might result in a significant reduction in heat exchanging performance due to leakage of the coolant.

Thus, in order to prevent a reduction in heat exchanging performance due to leakage of the coolant in such a facility apparatus, it is necessary to inhibit corrosion of the metal material, such as a pipe, of the system, or to adequately control the concentration of the corrosion inhibitor so as to prevent a reduction in the corrosion protection performance of the coolant.

Accordingly, there has been proposed a corrosion monitoring device. In order to inhibit corrosion of a metal material of an electronic apparatus in an atmosphere containing moisture, the corrosion monitoring device includes a simulation electrode made of the same material as the electronic apparatus, and is configured to measure the corrosion rate of the simulation electrode by an impedance measurement, and thus monitor the corrosion state of the electronic apparatus (see, for example, Patent Literature 1).

Also, there has been proposed a corrosion environment quantification apparatus. In order to inhibit corrosion of a metal material used in an electronic device of a cooling apparatus using a high electrical insulating refrigerant, the corrosion environment quantification apparatus measures the impedance of an electrode provided on an electronic device substrate in a refrigerant circulation path, and thereby quantifies the corrosion environment of the cooling apparatus (see, for example, Patent Literature 2).

CITATION LIST

Patent Literature

Patent Literature 1: Japanese Unexamined Patent Application Publication No. 2-291952 (claim 1; page 3, lower left column to page 4, lower left column; and FIG. 1)

Patent Literature 2: Japanese Unexamined Patent Application Publication No. 5-126776 (paragraphs [0019] to [0025])

SUMMARY OF INVENTION

Technical Problem

The technique disclosed in Patent Literature 1 evaluates the corrosion rate by performing an electrochemical impedance measurement on an object electrode. Since the technique disclosed in Patent Literature 1 performs detection and determination on the basis of the magnitude of the reaction resistance of the electrode, the reaction needs to proceed to a certain extent, that is, the electrode surface needs to be corroded. In particular, in the case of a system having a high corrosion rate, the amount of corrosion damage is large. Therefore, adding the corrosion inhibitor again is not a sufficient solution, and it is not possible to inhibit corrosion of the system.

The technique disclosed in Patent Literature 2 can detect a reduction in corrosion protection performance, because a reduction in corrosion protection performance in a high electrical insulating refrigerant having high resistance appears as a significant change in the form of a reduction in resistance. With the technique disclosed in Patent Literature 2, however, in the case of a coolant whose resistance is reduced by addition of a corrosion inhibitor or an antifreeze, the change in the resistance value corresponding to a reduction in the concentration of the corrosion inhibitor is small, so that it is difficult to detect a reduction in corrosion protection performance.

Further, the resistance value of a coolant to which salt, such as a corrosion inhibitor, is added has a temperature dependency. More specifically, even in the case of a coolant having the same concentration, the resistance of the coolant decreases when the temperature increases, and the resistance increases when the temperature decreases. Accordingly, in the case of managing the corrosion performance by detecting a change in the resistance of the coolant, it is necessary to separately install a resistance compensation function corresponding to the temperature of the coolant. Therefore, the cost of installation and the installation space need to be taken into consideration.

The present invention aims to solve at least one of the aforementioned problems. The first object is to provide a corrosion protection performance degradation detection sensor that detects degradation (reduction in the concentration) of a corrosion inhibitor with high accuracy and high sensitivity on the basis of a change in the impedance of an electrode surface film.

Further, the second object is to provide a hot-water supply heating system and a facility apparatus each provided with a corrosion protection performance degradation detection sensor that appropriately controls the timing of adding a corrosion inhibitor to a coolant, and thus suppresses corrosion of a pipe.

Solution to Problem

A corrosion protection performance degradation detection sensor according to the present invention is a corrosion protection performance degradation detection sensor that detects a change in concentration of a corrosion inhibitor, which inhibits corrosion of an anticorrosion target material, added and contained in a solvent. The corrosion protection performance degradation detection sensor includes a detection electrode that reacts with the corrosion inhibitor dissolved in the solvent and forms on a surface thereof an electrode surface film which inhibits corrosion; a counter electrode that is disposed so as to face the detection electrode with a predetermined distance therebetween; and an AC power supply that applies an AC voltage with a predetermined frequency and a predetermined voltage between the detection electrode and the counter electrode; wherein a change in concentration of the corrosion inhibitor in the solvent is detected, on a basis of a change in impedance of the electrode surface film formed on a detection electrode surface at the time when the AC voltage with the predetermined frequency and the predetermined voltage is applied between the detection electrode and the counter electrode.

Advantageous Effects of Invention

According to the present invention, since a change in the concentration of a corrosion inhibitor in a solvent is detected, on the basis of a change in the impedance of an electrode surface film formed on a detection electrode surface, it is possible to detect degradation (reduction in the concentration) of the corrosion inhibitor with high accuracy and high sensitivity.

Further, it is possible to appropriately control the timing of adding a corrosion inhibitor to a coolant, and thus to inhibit corrosion of a pipe of a hot-water supply heating system and a facility apparatus.

DESCRIPTION OF EMBODIMENTS

Hereinafter, embodiments of the present invention will be described with reference to the drawings.

Embodiment 1

Figure 1:
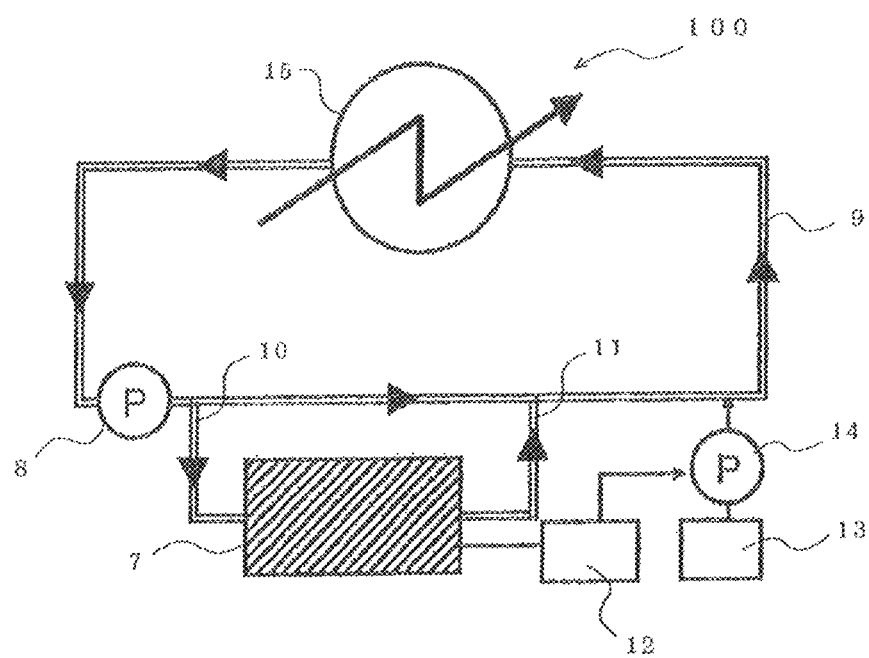
FIG. 1 illustrates an exemplary schematic configuration of a hot-water supply heating system provided with a corrosion protection performance degradation detection sensor according to Embodiment 1 of the present invention.
Figure 2:
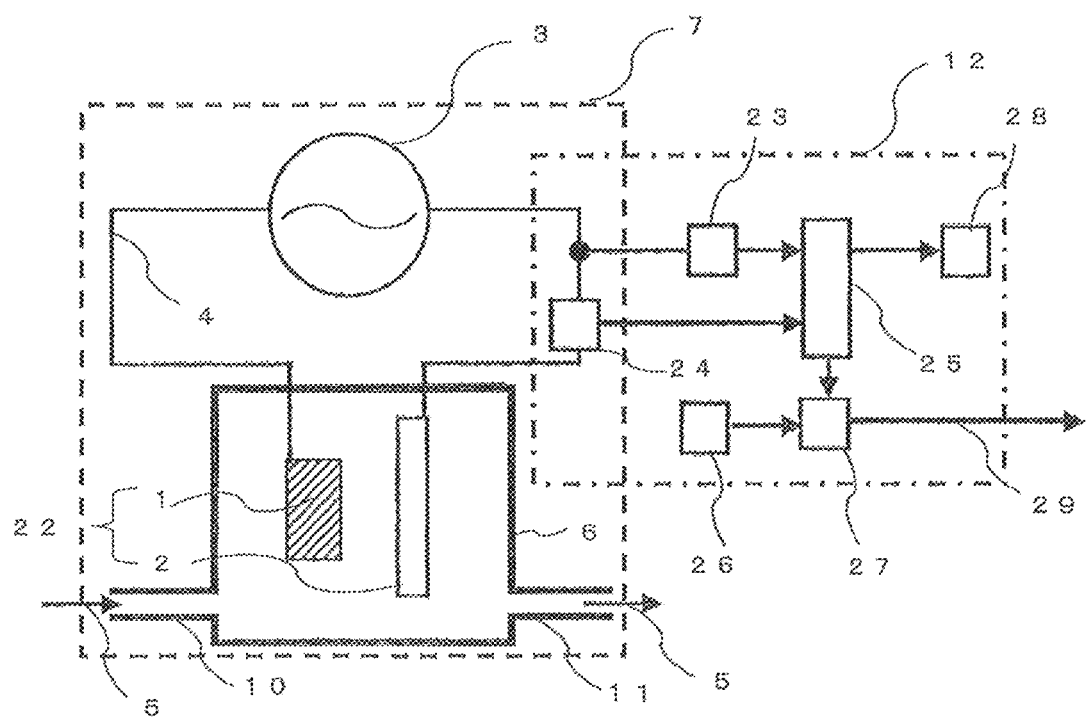
FIG. 2 illustrates an exemplary schematic configuration of the corrosion protection performance degradation detection sensor and a controller of FIG. 1.

FIG. 1 illustrates an exemplary schematic configuration of a hot-water supply heating system 100 provided with a corrosion protection performance degradation detection sensor 7 according to Embodiment 1 of the present invention. FIG. 2 illustrates an exemplary schematic configuration of the corrosion protection performance degradation detection sensor and a controller of FIG. 1. Note that a portion encircled by a dashed line in FIG. 2 corresponds to the corrosion protection performance degradation detection sensor 7 of FIG. 1, and a portion encircled by a dashed-dotted line corresponds to a controller 12 of FIG. 1.

The corrosion protection performance degradation detection sensor 7 is provided in a facility apparatus such as the hot-water supply heating system 100, for example. The corrosion protection performance degradation detection sensor 7 detects the concentration of a corrosion inhibitor contained in a coolant 5 (solvent) circulating through a pipe of the facility apparatus.

(Configuration of Hot-Water Supply Heating System 100)

The hot-water supply heating system 100 is capable of, for example, supplying hot water to a bathroom, a washroom, and a kitchen, and heating rooms, by utilizing heat generated by a heat source.

As illustrated in FIG. 1, the hot-water supply heating system 100 includes a cooling target 15 including a heat exchanger, a circulation pump 8 that feeds the coolant 5, the corrosion protection performance degradation detection sensor 7 that detects the concentration of a corrosion inhibitor contained in the coolant 5, a circulation path 9 through which the coolant 5 circulates, bypass paths 10 and 11 each connected to the corrosion protection performance degradation detection sensor 7 while bypassing part of the circulation path 9, the controller 12 that receives information on the corrosion protection performance of the coolant 5 from the corrosion protection performance degradation detection sensor 7, a corrosion inhibitor injection control unit 13 that supplies a corrosion inhibitor to a below-described liquid feeding pump 14, and the liquid feeding pump 14 that supplies the corrosion inhibitor to the circulation path 9. Of these, the circulation pump 8, the circulation path 9, the bypass paths 10 and 11, and the cooling target 15 forming a circulation circuit of the coolant 5 are anticorrosion targets (anticorrosion target material). That is, components that are likely to be in contact with the coolant 5 are the anticorrosion targets.

Note that the corrosion protection performance corresponds to the concentration of the corrosion inhibitor contained in the coolant 5.

The cooling target 15 corresponds to indoor and outdoor heat exchangers that efficiently transfer heat between a high temperature object and a low temperature object, a fan coil that adjusts the temperature and humidity and sends air to an air-conditioned space using a fan, a radiator that releases excessive generated heat, a hot-water tank that stores the coolant 5 to be supplied and circulated, and so on. The cooling target 15 has one end connected to the suction side of the circulation pump 8, and the other connected to the discharge side of the circulation pump 8 and to the corrosion protection performance degradation detection sensor 7 through the bypass path 11.

The circulation pump 8 circulates the coolant 5 flowing through the circulation path 9 and the bypass paths 10 and 11. The circulation pump 8 has the suction side connected to the outlet side of the cooling target 15, and the discharge side connected to the inlet side of the cooling target 15 and to the corrosion protection performance degradation detection sensor 7 through the bypass path 10. The circulation pump 8 may preferably be a capacity-controllable pump, for example.

The corrosion protection performance degradation detection sensor 7 detects a change in the state of an electrode surface film formed on a below-described detection electrode 1 associated with degradation of the corrosion protection performance by using electrochemical impedance measurement, and thereby detects the concentration of a corrosion inhibitor contained in the coolant 5. The corrosion protection performance degradation detection sensor 7 has one end connected to the discharge side of the circulation pump 8 through the bypass path 10 and the other end connected to the inlet side of the cooling target 15 through the bypass path 11. The corrosion protection performance degradation detection sensor 7 will be described in detail in "Configuration of Corrosion Protection Performance Degradation Detection Sensor 7 and Controller 12".

The circulation path 9 is a pipe connecting the various types of devices. The circulation path 9 is connected to the corrosion protection performance degradation detection sensor 7 through the bypass paths 10 and 11, and is connected to the liquid feeding pump 14. Further, the cooling target 15 and the liquid feeding pump 14 are connected to the circulation path 9.

Each of the bypass paths 10 and 11 is a pipe that has one end connected to the circulation path 9 and the other end connected to the corrosion protection performance degradation detection sensor 7, and that bypasses part of the circulation path 9.

The below-described detection electrode 1 of the corrosion protection performance degradation detection sensor 7 is made of a material that is the same as the metal material used for the pipe and so on of the anticorrosion targets. As the metal material of the anticorrosion targets, copper, aluminum, stainless steel, or the like may preferably be employed, for example.

The controller 12 receives information on the corrosion protection performance of the coolant 5 from the corrosion protection performance degradation detection sensor 7, and controls the operation (start and stop) of the liquid feeding pump 14 on the basis of the information on the corrosion protection performance. The control operation will be described in detail in "Configuration of Corrosion Protection Performance Degradation Detection Sensor 7 and Controller 12".

The corrosion inhibitor injection control unit 13 is connected to the circulation path 9 through the liquid feeding pump 14, and supplies a corrosion inhibitor to the solvent (coolant 5) flowing through the circulation path 9. As illustrated in FIG. 1, the controller 12 and the corrosion inhibitor injection control unit 13 are provided separately from each other. However, the functions of the two components may be integrated into either one of the two components.

The liquid feeding pump 14 is connected to the circulation path 9, and supplies (adds), to the circulation path 9, the corrosion inhibitor supplied from the corrosion inhibitor injection control unit 13. The operation of the liquid feeding pump 14 is controlled by the controller 12.

(Configuration of Corrosion Protection Performance Degradation Detection Sensor 7 and Controller 12)

As illustrated in FIG. 2, the corrosion protection performance degradation detection sensor 7 includes an AC power supply 3, a lead 4 connecting the AC power supply 3 and electrodes 22, and a housing 6 accommodating the electrodes 22 and part of the lead 4. The corrosion protection performance degradation detection sensor 7 includes a pair of electrodes 22, and is configured such that the coolant 5 flowing through the circulation path 9 of the hot-water supply heating system 100 can flow therein. The corrosion protection performance degradation detection sensor 7 detects a change in the state of an electrode surface film associated with degradation of the corrosion protection performance, by using electrochemical impedance measurement in which an AC voltage is applied to the electrodes 22 and the resistance component (impedance) is extracted from the obtained current response. By detecting a change in the state of the electrode surface film, the corrosion protection performance degradation detection sensor 7 can detect the concentration of the corrosion inhibitor.

The electrodes 22 are for measuring the impedance between the electrodes including the electrodes 22. The electrodes 22 include the detection electrode 1 made of the same material as the circulation path 9 of the hot-water supply heating system 100, and a counter electrode 2 that applies a current to the detection electrode 1.

The detection electrode 1 is made of a material that is the same as the metal material used for the pipe of the circulation circuit of the coolant 5 (the anticorrosion targets) of the hot-water supply heating system 100. The detection electrode 1 may preferably be made of copper, aluminum, stainless steel, or the like, in accordance with the metal material used for the pipe of the circulation circuit of the coolant 5. The detection electrode 1 is immersed in the coolant 5 to which the corrosion inhibitor is added, and thus is covered on its surface with an electrode surface film (electrode surface film) having a thickness of about several tens of nanometers to several hundreds of nanometers.

The counter electrode 2 is an electrode for applying a current to the detection electrode 1 through the coolant 5. The counter electrode 2 is disposed so as to face the detection electrode 1 with a predetermined distance therebetween. The counter electrode 2 is made of a metal that has high chemical stability and is resistant to corrosion even if a current is applied. More specifically, the counter electrode 2 may preferably be made of an electrochemically noble metal (that is less likely to cause a chemical reaction on its own) such as gold, platinum, titanium, copper, and stainless steel.

The AC power supply 3 applies an AC voltage to the electrodes 22. The AC power supply 3 is connected to the electrodes 22 through the lead 4. The value of the applied AC voltage needs to be optimized. This is because, as the voltage increases, the electrode reaction more easily precedes although the current response sensitivity increases. In order to balance the current response sensitivity and suppression of the progress of the electrode reaction, the applied voltage is preferably equal to or greater than 10 mV and less than or equal to 100 mV.

The lead 4 connects the AC power supply 3 and the electrodes 22.

The housing 6 accommodates the electrodes 22 and part of the lead 4, and maintains an enclosed space so as not to introduce disturbance factors such as an increase in the electrical conductivity due to dissolution of carbon dioxide from the atmosphere. This allows the corrosion protection performance degradation detection sensor 7 to perform an impedance measurement with higher accuracy.

As illustrated in FIG. 2, the controller 12 includes an applied voltage detection unit 23, a current detection unit 24, a computing unit 25, a threshold setting unit 26, a control unit 27, and a display unit 28.

The applied voltage detection unit 23 detects an AC voltage applied to the electrodes 22 by the AC power supply 3, and transmits its voltage value to the computing unit 25.

The current detection unit 24 detects a current response to the AC voltage, and transmits its current value to the computing unit 25.

The computing unit 25 calculates an impedance of the electrodes 22, using the voltage value and the current value transmitted from the applied voltage detection unit 23 and the current detection unit 24.

The threshold setting unit 26 sets an upper limit and a lower limit as impedance thresholds for corrosion protection performance degradation. The thresholds for corrosion protection performance degradation will be described in detail in "Operation of Corrosion Protection Performance Degradation Detection Sensor 7 and Controller 12".

The control unit 27 compares the impedance calculated by the computing unit 25 with the impedance thresholds for corrosion protection performance degradation transmitted from the threshold setting unit 26, and transmits an ON/OFF control output 29 corresponding to the comparison result to the pump 14. That is, the control unit 27 transmits an ON output as the ON/OFF control output 29 to the pump 14 when the impedance falls below the threshold, and transmits an OFF output as the ON/OFF control output 29 to the pump 14 when the impedance exceeds the threshold. Thus, the control unit 27 controls the timing of starting and stopping injection of the corrosion inhibitor from the corrosion inhibitor injection control unit 13.

The display unit 28 displays the value of the impedance calculated by the computing unit 25. Note that it is not necessary to provide the display unit 28.

In Embodiment 1, the control unit 27 determines the injection timing of the corrosion inhibitor. However, the determination may be made manually. That is, when the value of the impedance output from the computing unit 25 is displayed on the display unit 28, the impedance thresholds for corrosion protection performance degradation and the calculated impedance values are compared on the basis of the displayed value. Thus, the pump 14 is manually turned ON when the calculated impedance value falls below the threshold, and the pump 14 is manually turned OFF when the calculated impedance value exceeds the threshold.

(Operation of Hot-Water Supply Heating System 100)

As mentioned above, in the hot-water supply heating system 100, the circulation pump 8 is connected to the circulation path 9 serving as a circulation path (pipe) through which the coolant 5 flows, and thus the coolant 5 circulates. Part of the coolant 5 fed from the discharge side of the circulation pump 8 flows through the bypass path 10 into the corrosion protection performance degradation detection sensor 7, which is connected to the circulation path 9 while bypassing part of the circulation path 9, and then flows again into the circulation path 9 through the bypass path 11. Further, the other part of the coolant 5 flows through the circulation path 9, and meets the coolant 5 flowing from the bypass path 11.

The corrosion protection performance degradation detection sensor 7 detects the corrosion protection performance of the coolant 5 having flowed therein through the bypass path 10, on the basis of an impedance measurement. The impedance measurement will be described in detail in "Operation of Corrosion Protection Performance Degradation Detection Sensor 7".

The controller 12 receives the detection result of the corrosion protection performance degradation detection sensor 7. Then, the controller 12 controls the operation of the liquid feeding pump 14, on the basis of the detection result. That is, the controller 12 controls the operation (start and stop) of the liquid feeding pump 14, on the basis of the upper limit and the lower limit of the resistance value (impedance) detected by the corrosion protection performance degradation detection sensor 7.

More specifically, when the corrosion protection performance of the coolant 5 degrades, and thus the electrode surface film formed on the detection electrode 1 of the corrosion protection performance degradation detection sensor 7 is broken down, an electrolyte (coolant 5) enters the broken part.

Thus, the resistance value at the point when the resistance (impedance) is reduced is set as a resistance lower limit (impedance lower limit). When the resistance value reaches the lower limit, the controller 12 starts the liquid feeding pump 14 so as to supply the corrosion inhibitor to the coolant 5.

When the corrosion inhibitor is supplied to the coolant 5, the broken part of the electrode surface film is restored, so that the resistance detected by the corrosion protection performance degradation detection sensor 7 increases. This increase in resistance continues until the electrode surface film is completely restored. Thus, the resistance value at the point when the increase in resistance stops is set as a resistance upper limit (impedance upper limit). When the resistance value exceeds the resistance upper limit, the controller 12 stops the liquid feeding pump 14 so as to stop supply of the corrosion inhibitor to the coolant 5.

The coolant 5 having been controlled to an appropriate corrosion protection performance by the supply of the corrosion inhibitor from the liquid feeding pump 14 flows into the cooling target 15 through the circulation path 9. Then, the coolant 5 having flowed through the cooling target 15 is fed into the suction side of the circulation pump 8.

With this cycle, the hot-water supply heating system 100 can appropriately control the concentration of the corrosion inhibitor in the coolant 5 and maintain the corrosion protection performance, on the basis of the impedance response of the electrodes 22 of the corrosion protection performance degradation detection sensor 7.

(Operation of Corrosion Protection Performance Degradation Detection Sensor 7 and Controller 12)

The corrosion protection performance degradation detection sensor 7 applies an AC voltage to the detection electrode 1 and the counter electrode 2, measures an electrochemical impedance by extracting the resistance component from the obtained current response, and detects a change in the state of an electrode surface film associated with degradation of the corrosion protection performance on the basis of the measurement result. That is, by detecting a change in the state of the electrode surface, the corrosion protection performance degradation detection sensor 7 can detect the concentration of the corrosion inhibitor.

The value of the resistance component extracted from the current response varies in accordance with the frequency level of the applied AC voltage. The term "high-frequency domain" as used in the following description refers to a domain higher than 1 kHz; the term "low-frequency domain" refers to a domain of 1 Hz or lower; and the term "intermediate-frequency domain" refers to the domain between these domains. As the resistance component extracted from the current response in the high-frequency domain, an electric resistance component (solution resistance) that does not involve electron transfer is detected.

On the other hand, as the frequency is shifted toward the low-frequency domain, as the resistance component extracted from the current response, a resistance component (charge transfer resistance) of electrode reaction that involves electron transfer and a resistance component (Warburg impedance) of chemical reaction dependent on diffusion of reactants that reach the electrode surface appear.

The corrosion protection performance degradation detection sensor 7 according to Embodiment 1 applies a voltage with a predetermined frequency to the electrodes 22 in order to detect degradation of the electrode surface film as a change in resistance. As the frequency of the applied AC voltage increases, the electrode reaction such as corrosion reaction on the surface of the electrodes 22 is further suppressed, so that it is possible to detect an electric resistance of the electrode surface film. However, the effect of solution resistance needs to be taken into account at the same time. Therefore, it is necessary to set the optimum value for the frequency.

The relationship between frequency and resistance change will be described in detail in "Frequency Dependence of Detected Impedance".

Note that, as mentioned above, the voltage value of the AC power supply 3 is set to a predetermined value. By setting the frequency and the AC voltage of the applied AC voltage to predetermined values, the extracted resistance value is made to correspond to the state of the electrode surface.

That is, in a period (corrosion inhibition period) in which the concentration of the corrosion inhibitor is maintained at an appropriate level and an electrode surface film that inhibits corrosion of the core of the detection electrode 1 is formed, the resistance value is high.

On the other hand, in a stage (pitting initiation period, pitting initiation state) in which the electrode surface film is gradually being broken down due to a reduction in the concentration of the corrosion inhibitor and the coolant 5 enters the broken part, the electrode surface film having a higher resistance than the solution resistance is broken down, and therefore the resistance value is reduced compared to that in the corrosion inhibition period. The resistance reduction due to degradation of the electrode surface film will be described in "Impedance Reduction due to Deterioration of Electrode Surface Film".

Further, in a stage (corroded region) in which the breakdown of the electrode surface film proceeds and pitting occurs, the core under the electrode surface film of the detection electrode 1 comes into contact with the coolant 5. Thus, the resistance value is further reduced compared to that in the corrosion initiation period, due to the effect of the resistance of the metal core having a lower resistance than the coolant 5.

When the electrode surface film is broken down and a corroded region in which pitting occurs is formed, even if the concentration of the inhibitor contained in the coolant 5 is controlled to an appropriate value by supplying the corrosion inhibitor, the electrode surface film is not restored and the corrosion proceeds. The reason for this is as follows. In the pitting initiation period, although the electrode surface film is broken down, the electrode surface broken part is restored due to being in contact with the coolant 5 as long as the coolant 5 has an appropriate corrosion protection performance. On the other hand, once pitting is formed, the coolant 5 containing the corrosion inhibitor does not reach inside the pitting, so that the anode reaction progresses. Thus, the corrosion reaction progresses under the acidic conditions due to hydrogen ion produced by hydrolysis with water, and therefore the occurrence of pitting cannot be suppressed even by adding the corrosion inhibitor.

In view of the above, in the controller 12, the detection point of a reduction in corrosion protection performance is set to the pitting initiation period. That is, the controller 12 obtains, in advance, the resistance value (impedance) at the time when the electrode surface film is in the pitting initiation period (pitting initiation state), as a lower limit. Then, when the resistance value (impedance) detected by the corrosion protection performance degradation detection sensor 7 falls below the lower limit, the controller 12 starts the liquid feeding pump 14 so as to supply the corrosion inhibitor to the coolant 5. Thus, the hot-water supply heating system 100 can appropriately control the timing of adding the corrosion inhibitor to the coolant 5, and it is therefore possible to inhibit corrosion of the anticorrosion targets.

Further, in the controller 12, the detection point of a complete restoration of the corrosion protection performance is set to the point when the increase in resistance stops. That is, the controller 12 obtains, in advance, a saturation value of increase of the resistance (impedance) of the electrode surface film at the time when the liquid feeding pump is in operation and the supply of the corrosion inhibitor continues, as an upper limit. Then, when the resistance value detected by the corrosion protection performance degradation detection sensor 7 reaches the upper limit, the controller 12 stops the liquid feeding pump 14 so as to stop supply of the corrosion inhibitor to the coolant 5. Thus, the hot-water supply heating system 100 can reduce the risk of excessive addition of the corrosion inhibitor to the coolant 5.

In Embodiment 1, the case where the liquid feeding pump 14 is controlled on the basis of the upper limit and the lower limit described above is illustrated. However, in view of the response time of the liquid feeding pump 14, the time lag of change in the concentration of the corrosion inhibitor, and so on, the operation of the liquid feeding pump 14 may be started before the resistance value falls below the lower limit, and the operation of the liquid feeding pump 14 may be stopped before the resistance reaches the upper limit. That is, the detection point of a reduction in corrosion protection performance is set to the pitting initiation period, and it is thus only necessary to control the concentration of the corrosion inhibitor contained in the coolant 5 such that a corroded region where the electrode surface film is broken down and pitting occurs is not formed.

(Frequency Dependence of Detected Impedance)

Figure 3:
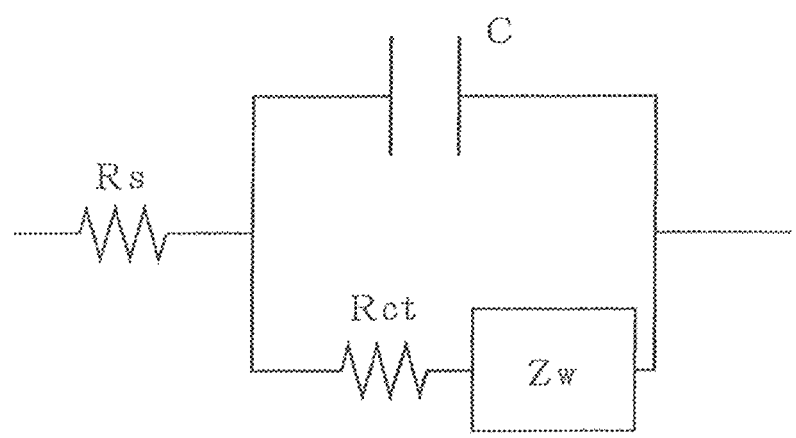
FIG. 3 illustrates an electrically equivalent circuit representing an electrode surface according to Embodiment 1 of the present invention.

In an electrochemical impedance measurement, an electrically equivalent circuit model simulating the electrode interface is created so as to evaluate the surface state and electrode reaction of an electrode. FIG. 3 illustrates a common electrically equivalent circuit simulating an electrode reaction on an electrode surface. An impedance Ztotal of the entire electrically equivalent circuit of FIG. 3 includes below-described C, Rs, Rct, and Zw. C is a capacity for forming an electric double layer, and is calculated taking into account the effect of the charge stored on the surface film. Rs is a solution resistance, and is calculated taking into account the electrolyte resistance, the copper electrode resistance, and the surface film resistance. Rct is a charge transfer resistance, and is a resistance component related to electron transfer in the electrode reaction. Zw is a Warburg impedance, and is a resistance component related to mass transfer and diffusive transfer in the electrode reaction. An AC voltage is applied to the electrically equivalent circuit of FIG. 3, and an impedance is detected from the obtained current response. For the detected impedance, the following formula dependent on an applied angular frequency $\omega$ holds.

[Math. 1]

$$Ztotal = Rs + \frac{1}{\frac{1}{Zc} + \frac{1}{Rct + Zw}} \quad (1)$$

$$Zc = (j\omega C) - 1 \quad (2)$$

From the formulas (1) and (2), the following formula is obtained.

[Math. 2]

$$Ztotal = Rs + \frac{1}{j\omega C + \frac{1}{Rct + Zw}} \quad (3)$$

In the formula (3), if $\omega \Rightarrow \infty$, Ztotal approaches Rs, and if $\omega \Rightarrow 0$, Ztotal approaches Rs+Rct+Zw. That is, this indicates that, information on the solution resistance is obtained in the high-frequency domain; information on the charge transfer resistance and Warburg impedance are obtained in the low-frequency domain, in addition to the solution resistance; and information on the capacity for forming an electric double layer is obtained in the intermediate-frequency domain, in addition to the solution resistance, charge transfer resistance, and Warburg impedance. In particular, the solution resistance other than the electrical resistance of the electrode surface film is included in the high-frequency domain, and the electrode reaction is likely to proceed due to a delay in polarity inversion of the applied AC voltage in the low-frequency domain, and therefore the frequency needs to be carefully determined when measuring the electrode surface film resistance. The correlation between the frequency during voltage application and the resistance change due to degradation of the electrode surface film will be described in detail in Embodiment 3.

(Coolant 5 (Solvent))

The coolant 5 flowing between the detection electrode 1 and the counter electrode 2 is an aqueous solvent flowing through the circulation path of the hot-water supply heating system 100. A corrosion inhibitor that inhibits corrosion of the metal of the anticorrosion targets and the detection electrode 1 is added to the coolant 5. Note that there may be cases that, in cold climates, an antifreeze is added so as to prevent the coolant 5 from freezing.

(Corrosion Inhibitor)

As the corrosion inhibitor, precipitation film type corrosion inhibitors such as benzotriazole and 8-quinolinol, adsorption film type corrosion inhibitors such as tetraalkylammonium, oxide film type corrosion inhibitors such as sodium nitrite, sodium molybdate, and sodium polyphosphate may be employed.

As the corrosion inhibitor, the most appropriate corrosion inhibitor selected in accordance with the material of the anticorrosion targets is preferably used. That is, if the anticorrosion targets are made of copper, a precipitation film type corrosion inhibitor such as benzotriazole may preferably be used, and if the anticorrosion targets are made of iron, an oxide film type corrosion inhibitor such as sodium nitrite may preferably be used.

Next, the corrosion protection mechanism of the surface of the detection electrode 1 by the corrosion inhibitor will be described. The metal of the detection electrode 1 is eluted into the coolant 5 and reacts with the corrosion inhibitor, so that an electrode surface film is formed on the surface of the detection electrode 1. When the electrode surface film is formed on the detection electrode, the detection electrode 1 is covered with the electrode surface film, so that further dissolution (elution) of the detection electrode 1 is suppressed.

Then, in the electrode surface film on the surface of the detection electrode 1, dissolution reaction and formation reaction of the detection electrode 1 are repeated. When these reactions are in equilibrium, metal elution from the detection electrode 1 is suppressed, and therefore the detection electrode 1 can exist stably. On the other hand, in the case where the concentration of the corrosion inhibitor contained in the coolant 5 decreases due to decomposition of the corrosion inhibitor, or in the case where a corrosive ion that corrodes the detection electrode 1 is mixed, the equilibrium state is broken, and the dissolution reaction becomes dominant. As a result, the corrosion reaction proceeds.

Next, the reaction of the surface of the detection electrode 1 with the corrosion inhibitor will be described.

For example, it is assumed that the pipe of the anticorrosion targets is made of copper, and that the detection electrode 1 of the corrosion protection performance degradation detection sensor 7 is also made of copper. Further, it is assumed that the coolant 5 circulating in the hot-water supply heating system 100 is an aqueous solvent, and that propylene glycol as an antifreeze and benzotriazole (BTAH) as a copper corrosion inhibitor are added to the coolant 5.

Benzotriazole is disassociated in the coolant 5 by the following reaction, and thus becomes anion $BTA^-$. Then, anion $BTA^-$ forms a complex, together with copper ion $Cu^+$ dissolved in the coolant 5, so that a precipitation film $[Cu-BTA]_n$ of uncharged polymer complex is formed on the copper surface.

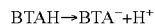

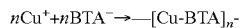

This precipitation film becomes an electrode surface film, and thus inhibits corrosion of the metal, which is copper, of the hot-water supply heating system.

(Impedance Reduction Due to Deterioration of Electrode Surface Film)

The correlation between the electrode surface film formed by the corrosion inhibitor and the impedance will be described using a simplified model of FIG. 4 of an electrode with an electrode surface film formed thereon. The simplified model of FIG. 4 includes an electrode surface film represented by a dielectric body having a permittivity $\in$ and a thickness I, and an electrolyte having a greater $\in$ value than the electrode surface film, for an electrode having an electrode area A. The resistance change of the electrode surface film in the impedance measurement can be well represented by a capacity component (capacitance). For the capacitance of this system, the following formula holds.

[Math. 3]

$$C = \frac{\varepsilon A}{\ell} \quad (4)$$

Figure 4:
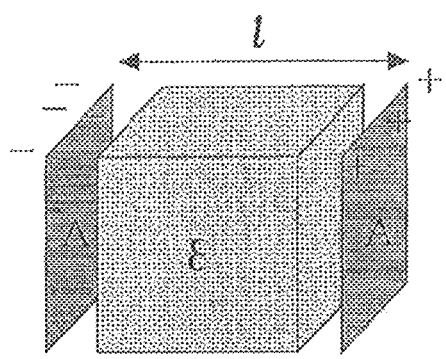
FIG. 4 illustrates a simplified model representing an electrode surface film formed on the electrode surface according to Embodiment 1 of the present invention.

It is assumed that, in the electrode-electrode surface film model of FIG. 4, when the electrode surface film of the electrode surface degrades, the film thickness decreases, or the electrode surface film becomes porous, and the electrolyte enters the pores.

When the film thickness decreases, the thickness I of the dielectric body representing the electrode surface film decreases. Further, it is assumed that the surface area increase due to the porous film, and the electrolyte having a high permittivity enters the pores. In this case, both $\in$ and A increase. In any case, it is understood that the capacitance C of the system in the formula (4) increases. When C increases, Zc and Ztotal in formulas (2) and (3) decrease.

That is, this indicates that when the electrode surface film degrades with a reduction in the corrosion protection performance of the coolant, the detected impedance decreases. (Impedance Measurement of Electrode Surface)

Figure 5:
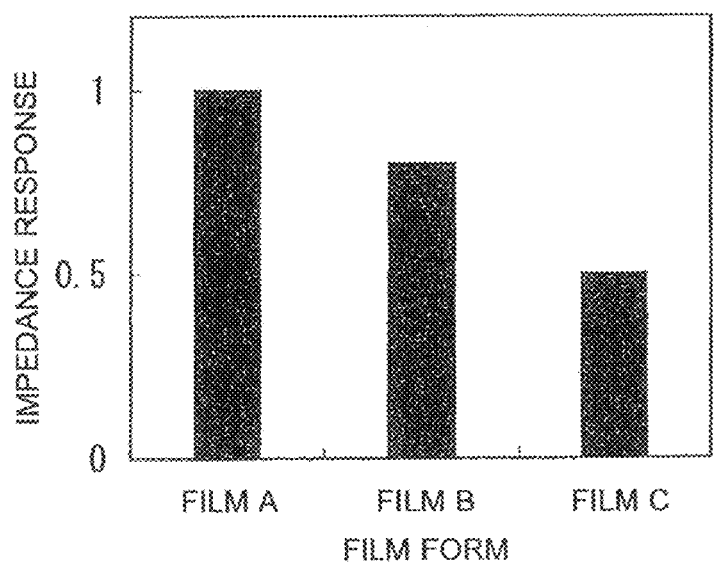
FIG. 5 is a graph illustrating the impedance response with respect to the film form of a detection electrode of the corrosion protection performance degradation detection sensor of FIG. 2.

FIG. 5 is a graph illustrating the impedance response with respect to the film form of the detection electrode 1 of the corrosion protection performance degradation detection sensor 7 of FIG. 2. FIG. 5 shows the correlation between the film form of the electrode surface film and the impedance response of the corrosion protection performance degradation detection sensor 7. Note that, an AC voltage of 10 mV at a frequency of 100 Hz was applied to the electrodes 22, and the impedance response was detected. Further, in FIG. 5, the value of the impedance response is calculated assuming that the value of the impedance response to an electrode surface film A (described below) is 1.

As the coolant 5 filled in the housing 6 of the corrosion protection performance degradation detection sensor 7, three types of coolants 5 were prepared: a coolant 5A to which benzotriazole was added at a concentration high enough to prevent corrosion of copper, a coolant 5B to which benzotriazole was added at a concentration at which breakdown of the copper electrode surface film initiates, and a coolant 5C to which benzotriazole was added at a concentration at which the copper electrode core is exposed. The forms of the electrode surface films A through C correspond to these coolants 5A through 5C, respectively.

That is, the electrode surface film A which is a dense electrode surface film was formed by the coolant 5A having a high concentration of corrosion inhibitor; the electrode surface film B in a state in which breakdown of the surface film is initiated was formed by the coolant 5B having a lower concentration; and the electrode surface film C in a state in which the electrode core is exposed under the surface film was formed by the coolant 5C having a further lower concentration.

It is found from FIG. 5 that the impedance responses corresponding to the forms of the electrode surface films are detected, and that as the benzotriazole concentration in the coolant 5 decreases and the breakdown of the electrode surface film proceeds, the resistance value of the electrode decreases.

Further, after measuring the impedance response, a sufficient amount of benzotriazole was added to the coolants 5B and 5C, and changes in electrode surface resistance were examined. Then, the resistance value provided by the coolant 5B was increased to the resistance value of the electrode surface provided by the coolant 5A. However, the electrode surface resistance provided by the coolant 5C remained low. This showed that when the breakdown of the electrode surface proceeds and thus pitting proceeds until the copper core is exposed, even if benzotriazole as a corrosion inhibitor is added, the electrode surface film is not restored. That is, once the anticorrosion targets corrode and the copper core is exposed, restoration is not possible even if a corrosion inhibitor is added.

Further, separately from the impedance measurement described above, the electrode potential of the detection electrode 1 was measured for each of the coolants 5A through 5C. Then, it was found that as the benzotriazole concentration in the coolant 5 decreases and the breakdown of the electrode surface film proceeds, the electrode potential decreases. The electrode potential indicates the breakdown state of the electrode surface film. More specifically, when the electrode surface is covered with a complete electrode surface film, the electrode potential is high due to the effect of the electrode surface film having a high potential. However, when the benzotriazole concentration decreases and the electrode surface film begins to be broken down, the effect of the underlying copper core appears, so that the potential decreases. Then, when the electrode surface film is broken down so that the copper core is exposed, the electrode potential becomes extremely near to the same potential.

As described above, the corrosion protection performance degradation detection sensor 7 according to Embodiment 1 applies an AC voltage with a predetermined frequency and a predetermined voltage to the detection electrode 1 on which the electrode surface film is formed and the counter electrode 2, and extracts the resistance component (impedance) from the obtained current response. Thus, since the resistance component is mainly the electrical resistance component (solution resistance) that does not involve electron transfer, the corrosion protection performance degradation detection sensor 7 according to Embodiment 1 can detect degradation (reduction in the concentration) of the corrosion inhibitor as a change in electrode film resistance with high accuracy and high sensitivity. Accordingly, it is obvious that even in the case of, for example, a coolant 5 having a reduced resistance due to addition of antifreeze or the like, it is possible to detect degradation of corrosion protection performance.

Further, as described above, the corrosion protection performance degradation detection sensor 7 detects degradation (reduction in the concentration) of the corrosion inhibitor with high accuracy and high sensitivity from a change in the formation state of the electrode surface film formed on the detection electrode 1, and the controller 12 sets the detection point of a reduction in corrosion protection performance to the pitting initiation period. That is, the hot-water supply heating system 100 according to Embodiment 1 can appropriately control the timing of adding the corrosion inhibitor to the coolant 5, and it is therefore possible to inhibit corrosion of the anticorrosion targets.

Embodiment 2

The water quality (environment) of the coolant 5 flowing in the housing 6 of the corrosion protection performance degradation detection sensor 7 and the water quality of the coolant 5 circulating in the hot-water supply heating system 100 vary in accordance with the size of the bypass path 10, the bypass path 11, and the circulation pump 8 connected to the corrosion protection performance degradation detection sensor 7, and the housing 6. Thus, when the water quality (environment) of the coolant 5 flowing in the housing 6 of the corrosion protection performance degradation detection sensor 7 and the water quality of the coolant 5 circulating in the hot-water supply heating system 100 do not any longer correspond to each other, corrosion of the detection electrode 1 and corrosion of the circulation path of the hot-water supply heating system 100 do not any longer correspond to each other. Thus, it might become impossible to appropriately control the timing of adding the corrosion inhibitor to the circulation path of the hot-water supply heating system 100, and to inhibit corrosion.

In view of the above, a hot-water supply heating system 100 according to Embodiment 2 is configured taking into consideration that the environment to which the detection electrode 1 is exposed and the environment to which the anticorrosion targets of the hot-water supply heating system 100 are exposed are made substantially the same.

Note that, in Embodiment 2, the differences from Embodiment 1 will be mainly described. Further, the configuration of the corrosion protection performance degradation detection sensor 7 and the hot-water supply heating system 100 of Embodiment 2 is the same as that of Embodiment 1, and therefore will be described with reference to FIGS. 1 and 2.

The factors that affect corrosion of the detection electrode 1 and the anticorrosion targets of the hot-water supply heating system 100 include the temperature and flow rate of the coolant 5, dissolved oxygen level, corrosive ion, and concentration of the corrosion inhibitor. Note that, as the corrosion inhibitor added to the coolant 5, benzotriazole was employed as in the case of Embodiment 1.

In the housing 6 of Embodiment 2, the temperature and flow rate of the coolant 5 are set so as to achieve the same environment as that to which the anticorrosion targets are exposed, by adjusting the heat retaining system, the pumping rate, and dimensional design.

Further, the dissolved oxygen level (solubility) dependent on the temperature and flow rate of the coolant 5 are set so as to achieve the same environment as that to which the anticorrosion targets are exposed, by adjusting the temperature and flow rate of the coolant 5 as described above.

In this configuration, the concentrations of the corrosive ion and the corrosion inhibitor were measured in the environment to which the detection electrode 1 is exposed and the environment in the circulation path of the hot-water supply heating system 100. Note that, for the water quality survey of the coolant 5 flowing in the housing 6 of the corrosion protection performance degradation detection sensor 7, the samples of the coolant 5 were obtained while operating the hot-water supply heating system 100.

As for the corrosive ion, the measurement was focused on the corrosive ion that corrodes copper. Carbonate ion, sulfate ion, and chloride ion were selected as those that might be mixed during operation, and their concentrations were measured by ion chromatography analysis.

The concentration of the corrosion inhibitor contained in the coolant 5 was measured by ultraviolet absorption spectrometry.

The results of analysis of the samples of the coolant 5 showed that the concentration of each of the corrosive ion and the corrosion inhibitor was the same in the coolant 5 flowing through the corrosion protection performance degradation detection sensor 7 and the coolant 5 flowing through the anticorrosion targets.

That is, by setting the dimensional size of the bypass path 10, the bypass path 11, and the circulation pump 8 connected to the corrosion protection performance degradation detection sensor 7, and the housing 6 such that the coolant 5 flowing through the detection electrode 1 and the coolant 5 flowing through the anticorrosion targets have the same temperature and flow rate, it is possible to make the environment to which the detection electrode 1 is exposed and the environment in the circulation path of the hot-water supply heating system 100 substantially the same.

In this way, the hot-water supply heating system 100 according to Embodiment 2 can make the detection electrode 1 of the corrosion protection performance degradation detection sensor 7 reliably serve as a simulation electrode. Thus, the hot-water supply heating system 100 according to Embodiment 2 can appropriately control the timing of adding the corrosion inhibitor to the coolant 5, and it is therefore possible to inhibit corrosion of the anticorrosion targets of the hot-water supply heating system 100.

Embodiment 3

As mentioned above, as the frequency of the applied AC voltage decreases, the resistance component (impedance) of the electrode surface film of the corrosion protection performance degradation detection sensor 7 increases. This is because, as the frequency of the applied AC voltage is shifted from the high-frequency side to the low-frequency side, not only the resistance (solution resistance, including the resistance to electrical conduction in the electrode) corresponding to electrical conduction, but also the electrical resistance (charge transfer resistance) responsive to the electron transfer rate in the electrode, the impedance due to the capacity of the electric double layer formed by the charge stored on the electrode surface, and the diffusion resistance (Warburg impedance) responsive to the diffusion rate of the reactants that reach the electrode interface appear in the detected impedance. In the high-frequency domain, the impedance varies in accordance with not only a change in the electrode surface film, but also the design of the corrosion protection performance degradation detection sensor 7, that is, the inter-electrode distance between the detection electrode 1 and the counter electrode 2, the electrode area, and the liquid properties of the solution (coolant 5) disposed between the electrodes. Therefore, it is difficult to extract only the resistance change of the electrode surface film. Further, in the low-frequency domain, the impedance is greatly affected by the diffusion rate of the reactants in the solution other than the resistance change of the electrode surface film. Therefore, as in the case of the high-frequency domain, it is difficult to extract only the resistance change of the electrode surface film. That is, in order to appropriately detect a change in the resistance of the electrode surface film, it is necessary to optimize the frequency of the applied AC voltage.

In view of the above, a corrosion protection performance degradation detection sensor 7 according to Embodiment 3 and a hot-water supply heating system 100 provided with the corrosion protection performance degradation detection sensor 7 are configured taking into consideration the frequency of the AC voltage applied from the AC power supply 3.

Figure 6:
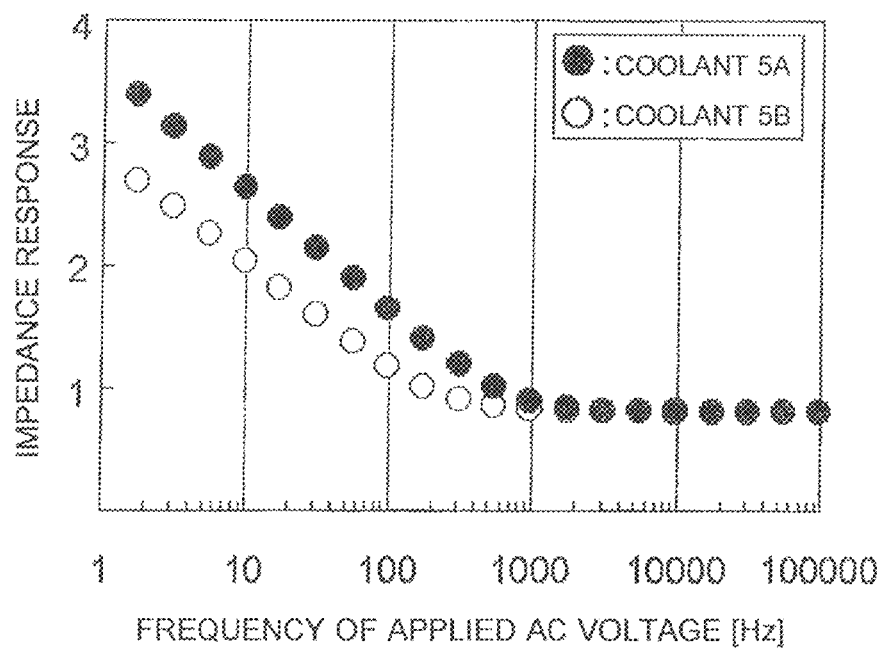
FIG. 6 is a graph illustrating the frequency dependence of impedance with respect to the applied AC voltage in a corrosion protection performance degradation detection sensor according to Embodiment 3 of the present invention.

FIG. 6 is a graph illustrating the frequency dependence of impedance with respect to the applied AC voltage in the corrosion protection performance degradation detection sensor 7 according to Embodiment 3 of the present invention. The impedance response varies in accordance with the electrode area (surface area) even in the case where the same material is used. Accordingly, FIG. 6 shows the resistance value at each frequency that is calculated assuming that the magnitude of the impedance response detected when the electrode surface (surface area) of the detection electrode 1 is normalized is 1. Further, in order to evaluate the effect of the impedance depending on the presence or absence of the inhibitor degradation, the above described coolants 5A and 5B were used. Note that, in Embodiment 3, the differences from Embodiments 1 and 2 will be mainly described.

As shown in FIG. 6, it was found that although the resistance component showed a substantially constant value in both the coolants when the frequency was in the high-frequency domain, the resistance component increased from a frequency near 1 kHz, and the degree of increase was smaller in the case of the coolant 5B. It is assumed that, in the high-frequency domain of 1 kHz or higher, because the solution resistance and other resistance factors related to the cell design have a great effect, the difference in the degradation of the electrode surface film does not easily appear, despite the difference in the concentration of the corrosion inhibitor between the coolant 5A and the coolant 5B. On the other hand, it is assumed that, in the low-frequency domain lower than 1 kHz, the degree of increase of the resistance with a shift to the low-frequency side is small due to the degradation of the corrosion protection performance of the coolant, so that the difference in the corrosion protection performance between the coolant 5A and the coolant 5B appears as the difference in resistance. That is, to make the degradation of the electrode surface film due to a reduction in corrosion protection performance appear as the difference in resistance, the upper limit of the frequency of the applied AC voltage may be set to 1 kHz or lower, preferably, 100 Hz or lower.

It was also found that when the frequency was further reduced to be lower than 1 Hz, the degree of increase of the coolant 5B was increased, so that the difference from the coolant 5A was reduced again (not shown). It is assumed that the difference between the two is reduced by the effect of the diffusion resistance representing the diffusion rate of the reactants in the coolant, rather than by the resistance change of the electrode surface film. That is, it is preferable to set the lower limit of the applied AC voltage to 1 Hz or higher.

Accordingly, when setting the upper limit of the applied AC voltage to 1 kHz or less, preferably 100 Hz or less, and the lower limit of the frequency to a range from 1 Hz or higher, and then monitoring the impedance response of the electrode surface at the set frequency, it is possible to make the impedance response of the corrosion protection performance degradation detection sensor 7 to correspond to the resistance change of the electrode surface film due to a reduction in corrosion protection performance. That is, since it is possible to make the impedance response to correspond to the resistance change of the electrode surface film by setting the frequency of the applied AC voltage as described above, the corrosion protection performance degradation detection sensor 7 according to Embodiment 3 can detect a change in the state of the electrode surface film formed on the detection electrode 1 with high accuracy and high sensitivity. Thus, it is possible to detect degradation (reduction in the concentration) of the corrosion inhibitor with high accuracy and high sensitivity. Accordingly, it is obvious that even in the case of, for example, a coolant having a reduced resistance due to addition of antifreeze or the like, it is possible to detect degradation of corrosion protection performance.

Further, as described above, the corrosion protection performance degradation detection sensor 7 detects degradation (reduction in the concentration) of the corrosion inhibitor with high accuracy and high sensitivity from a change in the state of the electrode surface film formed on the detection electrode 1, and the controller 12 sets the detection point of a reduction in corrosion protection performance to the pitting initiation period. That is, the hot-water supply heating system 100 according to Embodiment 3 can appropriately control the timing of adding the corrosion inhibitor to the coolant 5, and it is therefore possible to inhibit corrosion of the anticorrosion targets.

Embodiment 4

The impedance detected by the corrosion protection performance degradation detection sensor 7 remains almost unchanged until the applied AC voltage is below a certain predetermined value, but changes when the value becomes equal to or greater than the certain predetermined value. With the applied voltage, a driving force is generated that attracts the reactants in the electrolyte (coolant in Embodiment 4) in contact with the electrode surface to the electrode surface. As the applied voltage increases, the driving force increases, and therefore the electrode reaction occurs more easily, which results in reduced reaction resistance. Accordingly, it is necessary to set an upper limit for the voltage value of the applied AC voltage. Further, in order to detect the impedance, a predetermined voltage is applied to the system, and a current responsive to the voltage value is detected. Thus, the impedance of the system is calculated. If the voltage value of the applied AC voltage is small, although the impedance does not change, the current value for detecting the impedance is small. This leads to problems that the cost is needed to provide an amplifier for detecting the current, and that an accurate measurement cannot be made due to small noise being mixed. Accordingly, it is necessary to set a lower limit for the voltage value of the applied AC voltage.

In view of the above, a corrosion protection performance degradation detection sensor 7 according to Embodiment 4 and a hot-water supply heating system 100 provided with the corrosion protection performance degradation detection sensor 7 are configured taking into consideration the range of the upper limit and the lower limit of the voltage value of the applied AC voltage.

Figure 7:
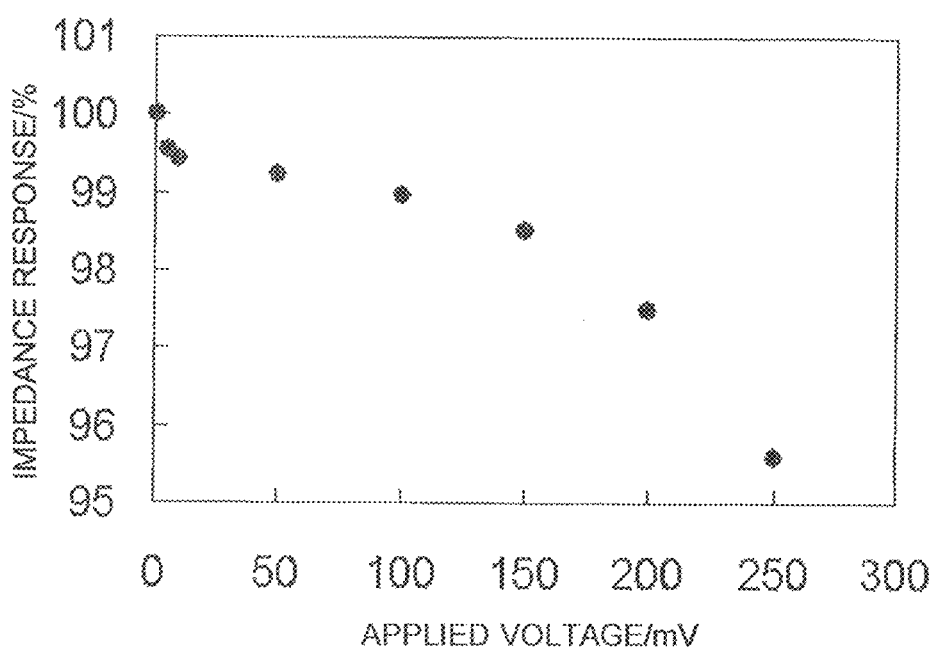
FIG. 7 is a graph illustrating the impedance response with respect to the applied AC voltage in a corrosion protection performance degradation detection sensor according to Embodiment 4 of the present invention.

FIG. 7 is a graph illustrating the impedance response with respect to the applied AC voltage in the corrosion protection performance degradation detection sensor 7 according to Embodiment 4 of the present invention. As mentioned above, as the voltage value of the applied AC voltage increases, the impedance response decreases. FIG. 7 plots the impedance at each voltage value, which is calculated assuming that the magnitude of the impedance response detected at an AC voltage of 1 mV is 100%. In order to evaluate the electrode surface impedance that is observed when a corrosion protection film is fully formed, the above-described coolant 5A was used. Further, the frequency of the applied AC voltage was set to 100 Hz.

Note that, in Embodiment 4, the differences from Embodiments 1 through 3 will be mainly described.

As shown in FIG. 7, it is found that when the voltage value is high, the impedance value responsive thereto is reduced, and when the voltage value is 150 mV or higher, the impedance response does not match (is equal to or less than 99% of) the impedance response that is obtained when an AC voltage of 1 mV is applied. That is, in order to obtain an accurate impedance response, the upper limit of the voltage value is preferably set to be less than 150 mV, and more preferably 100 mV or less.

On the other hand, when the lower limit of the voltage value is less than 10 mV, the detected current is reduced as described above. Accordingly, in some cases, it might be necessary to detect a current in the order of microamperes or less. Detection of a current in the order of microamperes requires an amplifying device to be newly installed and involves the risk of picking up small noise. Thus, there arises a problem of realization of an inexpensive high-precision detection sensor. Accordingly, the lower limit of the voltage value that realizes an inexpensive high-precision detection sensor is preferably 10 mV or greater.

Embodiment 5

The resistance value of the electrode surface film of the corrosion protection performance degradation detection sensor 7 varies in accordance with the surface area of the detection electrode 1 with respect to the counter electrode 2. That is, by optimizing the electrode area of the detection electrode 1 of the corrosion protection performance degradation detection sensor 7, it is possible to detect a change in electrode surface resistance with higher accuracy and higher sensitivity.

In view of the above, a corrosion protection performance degradation detection sensor 7 according to Embodiment 5 and a hot-water supply heating system 100 provided with the corrosion protection performance degradation detection sensor 7 are configured taking into consideration the surface area of the detection electrode 1 with respect to the counter electrode 2.

Figure 8:
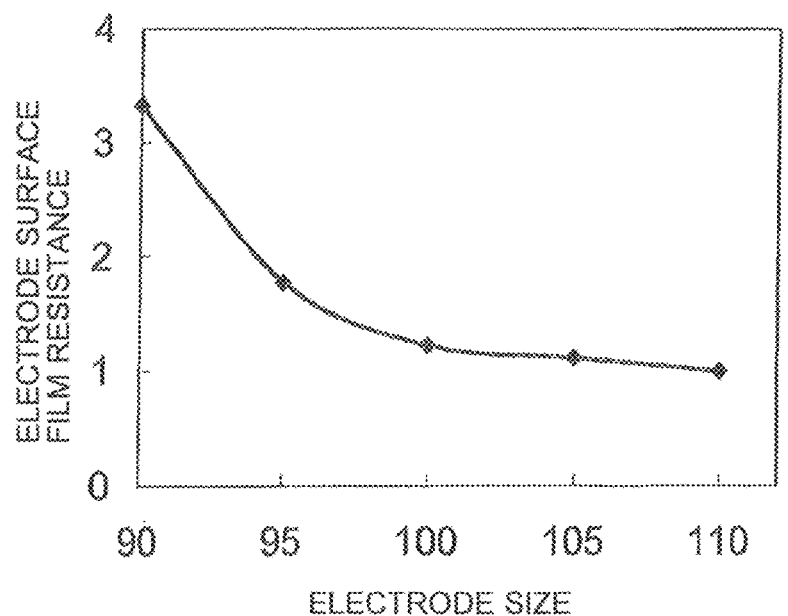
FIG. 8 is a graph illustrating the resistance value of the electrode surface film with respect to the electrode size of a corrosion protection performance degradation detection sensor according to Embodiment 5 of the present invention.

FIG. 8 is a graph illustrating the resistance value of the electrode surface film with respect to the electrode size of the corrosion protection performance degradation detection sensor 7 according to Embodiment 5 of the present invention. As the detection electrode 1 of the corrosion protection performance degradation detection sensor 7 that is described with reference to FIG. 1, below-described five types of detection electrodes 1 were prepared. Then, the resistance value of each electrode surface film was measured.

Size 1: a detection electrode 1 having a greater surface area corresponding to 110% of that of the counter electrode 2.

Size 2: a detection electrode 1 having a greater surface area corresponding to 105% of that of the counter electrode 2.

Size 3: a detection electrode 1 having the same surface area as the counter electrode 2.

Size 4: a detection electrode 1 having a smaller surface area corresponding to 95% of that of the counter electrode 2.

Size 5: a detection electrode 1 having a smaller surface area corresponding to 90% of that of the counter electrode 2.

Note that, the design is made such that the distance from the counter electrode 2 and the temperature of the coolant 5 are constant, and thus the solution resistance of the coolant 5 between the detection electrode 1 and the counter electrode 2 is controlled to be constant. Then, in this controlled state, an AC voltage was applied to the five types of electrodes, and the resistance value of the electrode surface film was calculated from the obtained current response. Note that, in FIG. 8, the value of the surface area (electrode size) of the detection electrode 1 is calculated assuming that the surface area of the counter electrode 2 is 100, and the value of the electrode surface resistance is calculated assuming that the resistance of the detection electrode 1 of the size 1 is 1.

Note that, in Embodiment 5, the differences from Embodiments 1 through 4 will be mainly described.

As shown in FIG. 8, it was found that the resistance value of the electrode surface film is increased by reducing the surface area of the detection electrode 1. In particular, when the surface area of the detection electrode 1 was equal to or less than 95% of the surface area of the counter electrode 2, the degree of increase became prominent. As the resistance of the electrode surface film increases, the value of the resistance change associated with the breakdown of the surface film due to a reduction in the corrosion protection performance of the coolant 5 increases. That is, as the resistance of the electrode surface film increases, the detection accuracy and sensitivity of the corrosion protection performance degradation detection sensor 7 can be increased.

In view of the above, in the corrosion protection performance degradation detection sensor 7 according to Embodiment 5, the surface area of the detection electrode 1 is set to be less than the surface area of the counter electrode 2, and is preferably set to be equal to or less than 95% of the surface area of the counter electrode 2.

With this configuration, it is possible to detect a change in the state of the electrode surface film formed on the detection electrode 1 with high accuracy and high sensitivity. Thus, it is possible to detect degradation (reduction in the concentration) of the corrosion inhibitor with high accuracy and high sensitivity. Accordingly, it is obvious that even in the case of, for example, a coolant having a reduced resistance due to addition of antifreeze or the like, it is possible to detect degradation of corrosion protection performance.

Further, as described above, the corrosion protection performance degradation detection sensor 7 detects degradation (reduction in the concentration) of the corrosion inhibitor with high accuracy and high sensitivity from a change in the state of the electrode surface film formed on the detection electrode 1, and the controller 12 sets the detection point of a reduction in corrosion protection performance to the pitting initiation period. That is, the hot-water supply heating system 100 according to Embodiment 5 can appropriately control the timing of adding the corrosion inhibitor to the coolant 5, and it is therefore possible to inhibit corrosion of the anticorrosion targets.

Embodiment 6

The solution resistance of the coolant 5 between the detection electrode 1 and the counter electrode 2 is determined from the surface area of the detection electrode 1, the conductivity of the coolant 5, and the distance between the detection electrode 1 and the counter electrode 2. Each of the surface area of the detection electrode 1 and the conductivity of the coolant 5 can be set to a predetermined value. Accordingly, by optimizing the distance between the detection electrode 1 and the counter electrode 2, it is possible to control the solution resistance of the coolant 5. In view of the above, a corrosion protection performance degradation detection sensor 7 according to Embodiment 6 and a hot-water supply heating system 100 provided with the corrosion protection performance degradation detection sensor 7 are configured taking into consideration the distance between the detection electrode 1 and the counter electrode 2. Note that, as for the setting of the inter-electrode distance, the inter-electrode distance was normalized by the ratio to the equivalent diameter of the detection electrode. The equivalent diameter is a representative diameter of the electrode that is used in place of the diameter of the circle in the case where the shape of the electrode is not a circle, and can be expressed by the following formula.

$$De = 4A/Lp$$

in which De is the equivalent diameter of the detection electrode, A is the electrode area, and Lp is the electrode periphery length. The inter-electrode distance was controlled by the equivalent diameter De.

Figure 9:
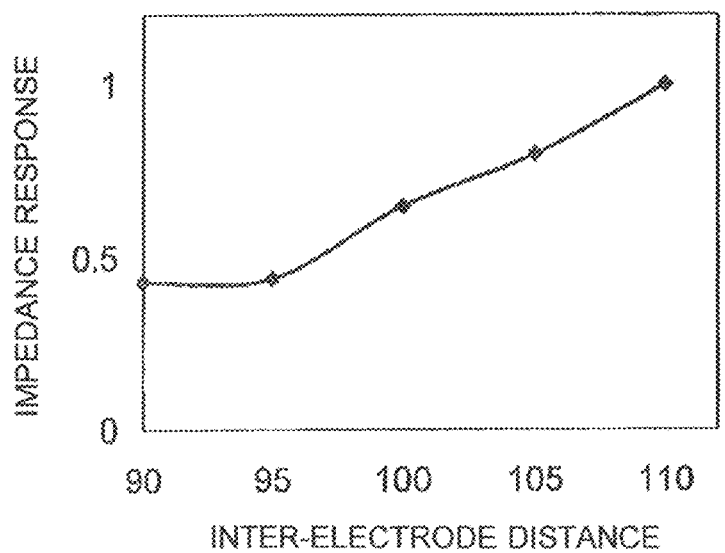
FIG. 9 is a graph illustrating the impedance response with respect to the inter-electrode distance of a corrosion protection performance degradation detection sensor according to Embodiment 6 of the present invention.

FIG. 9 is a graph illustrating the impedance response with respect to the inter-electrode distance of the corrosion protection performance degradation detection sensor 7 according to Embodiment 6 of the present invention. The distance between the detection electrode 1 and the counter electrode 2 of the corrosion protection performance degradation detection sensor 7 that is described with reference to FIG. 1 was set to the following five different distances. Then, with the thus prepared corrosion protection performance degradation detection sensors 7, the resistance value of each electrode surface film was measured.

Distance 1: the distance was set to 110% of the equivalent diameter of the detection electrode 1.

Distance 2: the distance was set to 105% of the equivalent diameter of the detection electrode 1.

Distance 3: the distance is set to be equal to the equivalent diameter of the detection electrode 1.

Distance 4: the distance was set to 95% of the equivalent diameter of the detection electrode 1.

Distance 5: the distance was set to 90% of the equivalent diameter of the detection electrode 1.

Note that, the detection electrode 1 was designed to have a greater surface area than the counter electrode 2, thereby reducing the resistance of the electrode surface film of the detection electrode 1, and thus making it easier to detect the solution resistance between the electrodes when performing a measurement. In this state, the impedance was measured with the five different distances between the detection electrode 1 and the counter electrode 2. Note that, in FIG. 9, the value of the inter-electrode distance is calculated assuming that the equivalent diameter of the detection electrode 1 is 100, and the value of each impedance response is calculated assuming that the impedance response obtained when the inter-electrode distance is 1 is 1. Note that, in Embodiment 6, the differences from Embodiments 1 through 5 will be mainly described.

As shown in FIG. 9, it was found that the impedance response including the resistance of the electrode surface film is reduced by reducing the distance between the detection electrode 1 and the counter electrode 2. In particular, when the inter-electrode distance was equal to or less than 95% of the equivalent diameter of the detection electrode 1, the degree of reduction of the impedance response became prominent. Note that, as the resistance of the coolant 5 between the electrodes 22 decreases, the resistance of the electrode surface film with respect to the total resistance increases. That is, the value of the resistance change associated with the breakdown of the surface film due to a reduction in the corrosion protection performance of the coolant 5 increases with respect to a change in the total resistance value. Accordingly, as the resistance of the coolant 5 between the electrodes 22 decreases, the detection accuracy and detection sensitivity of the corrosion protection performance degradation detection sensor 7 can be increased.

In view of the above, in the corrosion protection performance degradation detection sensor 7 according to Embodiment 6, the distance between the detection electrode 1 and the counter electrode 2 is set to be less than the equivalent diameter of the detection electrode 1, and is preferably to be equal to or less than 95% of the equivalent diameter of the detection electrode 1.

With this configuration, it is possible to detect a change in the state of the electrode surface film formed on the detection electrode 1 with high accuracy and high sensitivity. Thus, it is possible to detect degradation (reduction in the concentration) of the corrosion inhibitor with high accuracy and high sensitivity. Accordingly, it is obvious that even in the case of, for example, a coolant having a reduced resistance due to addition of antifreeze or the like, it is possible to detect degradation of corrosion protection performance.

Further, as described above, the corrosion protection performance degradation detection sensor 7 detects degradation (reduction in the concentration) of the corrosion inhibitor with high accuracy and high sensitivity from a change in the state of the electrode surface film formed on the detection electrode 1, and the controller 12 sets the detection point of a reduction in corrosion protection performance to the pitting initiation period. That is, the hot-water supply heating system 100 according to Embodiment 6 can appropriately control the timing of adding the corrosion inhibitor to the coolant 5, and it is therefore possible to inhibit corrosion of the anticorrosion targets.

Embodiment 7

In the above-described Embodiments 1 through 6, an appropriate material was prepared as the counter electrode 2 for the detection electrode 1, and thus the degradation of the corrosion protection performance was detected by the impedance measurement. However, a part of the existing pipe, that is, the circulation path 9 or the bypass paths 10 and 11 can be used as the counter electrode 2.

A corrosion protection performance degradation detection sensor 7 according to Embodiment 7 evaluates the impedance response obtained in the case where a part of a bypass path 10 is used as a counter electrode 2 for a detection electrode 1.

Figure 10:
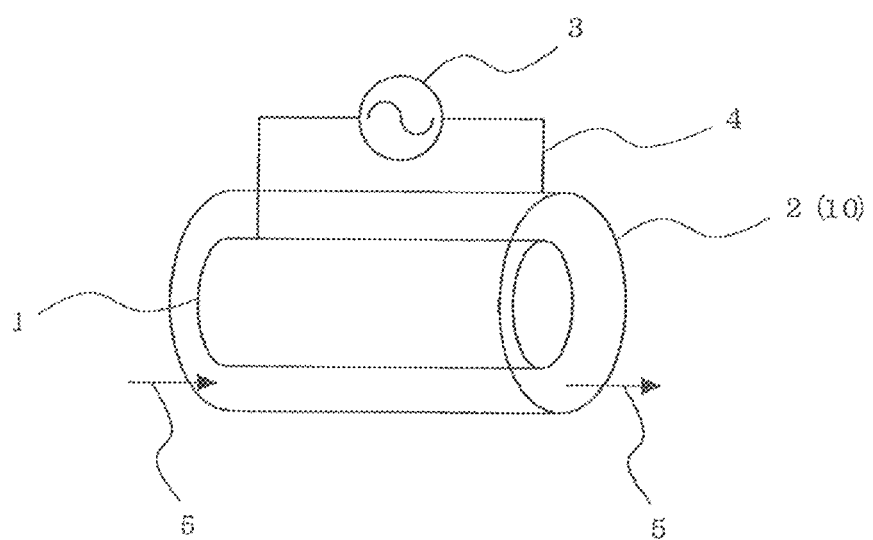
FIG. 10 illustrates an exemplary schematic configuration of a corrosion protection performance degradation detection sensor according to Embodiment 7 of the present invention.

FIG. 10 illustrates an exemplary schematic configuration of the corrosion protection performance degradation detection sensor 7 according to Embodiment 7 of the present invention. As illustrated in FIG. 10, a cylindrical electrode bar is used as the detection electrode 1 such that the detection electrode is equally distanced from the bypass path 10 formed of a circular pipe and serving as the counter electrode 2. Since the counter electrode 2 formed of a part of the bypass path 10 is disposed at the outer side of the detection electrode 1 formed of a cylindrical electrode bar, the counter electrode area is greater than the area of the detection electrode, and the counter electrode area increases as the inter-electrode distance increases. The inter-electrode distance was set to 95% of the equivalent diameter of the electrode bar serving as the detection electrode 1. Since a part of the existing pipe is used as the counter electrode 2, the coolant 5 flows between the detection electrode 1 and the counter electrode 2 (bypass path 10). Note that the detection electrode 1 and the lead 4 connected to the detection electrode 1 side is electrically insulated from the bypass path 10 serving as the counter electrode 2, and thus is designed not to be short-circuited.

The resistance change of the electrode surface film due to degradation of the corrosion protection performance of the coolant 5 was measured using the corrosion protection performance degradation detection sensor 7. Then, the result similar to the resistance change obtained in Embodiment 1 was obtained (not shown). It is assumed that, even in the case where the existing pipe was used as the counter electrode 2 as described above, it was possible to accurately detect degradation of the corrosion protection performance by appropriately controlling the inter-electrode distance from the detection electrode 1 and the electrode area of the detection electrode 1 and the counter electrode 2.

It is obvious that, in the above described Embodiments 1 through 7, the hot-water supply heating system 100 may be configured to notify the user of degradation of the corrosion protection performance with sound or the like when the corrosion protection performance degradation detection sensor 7 detects degradation of the corrosion protection performance of the coolant 5.

Further, since the corrosion protection performance degradation detection sensor 7 can detect degradation (reduction in the concentration) of the corrosion inhibitor with high accuracy and high sensitivity from a change in the state of the electrode surface film formed on the detection electrode 1, the hot-water supply heating system 100 does not have to manage the corrosion protection performance while detecting a change in the resistance of the coolant 5 or to separately install a resistance compensation function corresponding to the temperature of the coolant 5. That is, a cost increase due to managing the corrosion protection performance, separately installing a resistance compensation function corresponding to the temperature of the coolant 5, or the like is avoided.

Note that in the above-described Embodiments 1 through 7, the bypass paths 10 and 11 each bypassing part of the circulation path 9 and connected to the corrosion protection performance degradation detection sensor 7 is provided. However, the electrodes 22 (the detection electrode 1 and the counter electrode 2) may be disposed directly in the pipe of the circulation path 9 without providing a bypass.

It is obvious that features of Embodiments 1 through 7 may appropriately be combined with each other.

Further, the present invention may be applied to other facility apparatuses in which a solvent such as cooling water circulates.

For example, the present invention may be applied to facility apparatuses such as an air-conditioning system provided with a refrigeration cycle that is formed by connecting a compressor, a condenser, expansion means, an evaporator, and the like with a pipe and that circulates a refrigerant therein.

REFERENCE SIGNS LIST 1 detection electrode 2 counter electrode 3 AC power supply 4 lead 5 coolant 6 housing 7 corrosion protection performance degradation detection sensor 8 circulation pump 9 circulation path 10 bypass path 11 bypass path 12 controller 13 corrosion inhibitor injection control unit 14 liquid feeding pump 15 cooling target 22 electrode 23 applied voltage detection unit 24 current detection unit 25 computing unit 26 threshold setting unit 27 control unit 28 display unit 29 ON/OFF control output 100 hot-water supply heating system

The invention claimed is:

1. A facility apparatus comprising:
a circulation path through which a solvent circulates;
a liquid feeding pump that supplies a corrosion inhibitor to the circulation path, the corrosion inhibitor inhibiting corrosion of an anticorrosion target material forming the circulation path;
a detection electrode that reacts with the corrosion inhibitor dissolved in the solvent and forms on a surface thereof an electrode surface film which inhibits corrosion, the detection electrode is made of a material that is a same metal material used for the anticorrosion target material forming the circulation path;
a counter electrode that is disposed so as to face the detection electrode with a predetermined distance therebetween;
an AC power supply that applies an AC voltage with a predetermined frequency and a predetermined voltage between the detection electrode and the counter electrode; and
a controller that controls an operation of the liquid feeding pump on a basis of a change in impedance of the electrode surface film formed on a detection electrode surface at a time when the AC voltage with the frequency of less than 1 kHz and more than 1 Hz is applied between the detection electrode and the counter electrode,
wherein the controller is configured to
obtain, in advance, an impedance at a time when the electrode surface film of the detection electrode is in a pining initiation state, as a lower limit, and
start the liquid feeding pump when the impedance of the electrode surface film formed on the detection electrode surface falls below the lower limit.

2. The facility apparatus of claim 1, wherein the predetermined frequency of the AC voltage is equal to or less than 100 Hz.

3. The facility apparatus of claim 1, wherein the predetermined voltage of the AC voltage is a voltage in a range with an upper limit of 100 mV and a lower limit of 1 mV.

4. The facility apparatus of claim 1, wherein the detection electrode is configured such that a surface area thereof is less than a surface area of the counter electrode.

5. The facility apparatus of claim 4, wherein the detection electrode is configured such that the surface area thereof is equal to or less than 95% of the surface area of the counter electrode.

6. The facility apparatus of claim 1, wherein an inter-electrode distance between the detection electrode and the counter electrode is less than an equivalent diameter (De) of the detection electrode represented by a following formula:

$$De = 4A/Lp$$

in which A is a surface area of sides of the detection electrode, and Lp is a periphery length along a length and width of the detection electrode.

7. The facility apparatus of claim 6, wherein the inter-electrode distance between the detection electrode and the counter electrode is equal to or less than 95% of the equivalent diameter (De) of the detection electrode.

8. The facility apparatus of claim 1, further comprising:
a corrosion protection performance degradation detection sensor that includes the detection electrode and the counter electrode; and
a first and a second bypass path, each bypass path being connected to the corrosion protection performance degradation detection sensor while bypassing part of the circulation path.

9. A hot-water supply heating system comprising:
a corrosion protection performance degradation detection sensor including
a detection electrode that reacts with a corrosion inhibitor dissolved in a solvent and forms on a surface thereof an electrode surface film which inhibits corrosion, a counter electrode that is disposed so as to face the detection electrode with a predetermined distance therebetween, and an AC power supply that applies an AC voltage with a predetermined frequency and a predetermined voltage between the detection electrode and the counter electrode, the corrosion protection performance degradation detection sensor configured to detect a change in concentration of the corrosion inhibitor in the solvent, on a basis of a change in impedance of the electrode surface film formed on a detection electrode surface at a time when the AC voltage with the predetermined frequency and the predetermined voltage is applied between the detection electrode and the counter electrode, a cooling target that is heated or cooled by a solvent;

a circulation pump that circulates the solvent;

a circulation path to which the cooling target and the circulation pump are connected and through which the solvent circulates;

a bypass path that is connected to the corrosion protection performance degradation detection sensor while bypassing part of the circulation path;

a liquid feeding pump that supplies the corrosion inhibitor to the circulation path, the corrosion inhibitor inhibiting corrosion of an anticorrosion target material forming the circulation path and the bypass path; and a controller that controls an operation of the liquid feeding pump, on a basis of a detection result of the corrosion protection performance degradation detection sensor, wherein the controller is configured to obtain, in advance, an impedance at a time when the electrode surface film of the detection electrode is in a pitting initiation state, as a lower limit and start the liquid feeding pump when the impedance of the electrode surface film formed on the detection electrode surface at a time when the AC voltage with the predetermined frequency and the predetermined voltage is applied between the detection electrode and the counter electrode falls below the lower limit, wherein, the detection electrode is made of a material that is a same metal material used for the anticorrosion target material forming the circulation path.

10. The hot-water supply heating system of claim 9, wherein the controller is configured to obtain, in advance, a saturation value of increase of the impedance of the electrode surface film of the detection electrode at a time when the liquid feeding pump is in operation, as an upper limit and stop the liquid feeding pump when the impedance of the electrode surface film formed on the detection electrode surface at a time when an AC voltage with a predetermined frequency and a predetermined voltage is applied between the detection electrode and the counter electrode reaches the upper limit.

11. The hot-water supply heating system of claim 9, wherein the counter electrode is a part of a pipe of the bypass path; and wherein the detection electrode is disposed at a center of the pipe.

12. A facility apparatus comprising:

a circulation path through which a solvent circulates;

a liquid feeding pump that supplies a corrosion inhibitor to the circulation path, the corrosion inhibitor inhibiting corrosion of an anticorrosion target material forming the circulation path;

a detection electrode that reacts with the corrosion inhibitor dissolved in the solvent and forms on a surface thereof an electrode surface film which inhibits corrosion, the detection electrode is made of a material that is a same metal material used for the anticorrosion target material forming the circulation path;

a counter electrode that is disposed so as to face the detection electrode with a predetermined distance therebetween;

an AC power supply that applies an AC voltage with a predetermined frequency and a predetermined voltage between the detection electrode and the counter electrode; and a controller that controls an operation of the liquid feeding pump, on a basis of a change in impedance of the electrode surface film formed on a detection electrode surface at a time when the AC voltage with the predetermined frequency and the predetermined voltage is applied between the detection electrode and the counter electrode, wherein the controller is configured to obtain, in advance, an impedance at a time when the electrode surface film of the detection electrode is in a pitting initiation state, as a lower limit, and start the liquid feeding pump when the impedance of the electrode surface film formed on the detection electrode surface falls below the lower limit.

* * * * *